United States Patent [19]
Cohen et al.

[11] Patent Number: 5,785,694
[45] Date of Patent: Jul. 28, 1998

[54] INTERNAL URINARY CATHETER

[76] Inventors: Kenneth L. Cohen, 9 Bishop Dr.,
Woodbridge, Conn. 06525; Dennis J. Hanlon, 15 Morris Rd., East Haven, Conn. 06512

[21] Appl. No.: 566,356

[22] Filed: Dec. 1, 1995

[51] Int. Cl.$^6$ .................................................. A61M 5/00
[52] U.S. Cl. ............................................ 604/250; 604/101
[58] Field of Search ................................. 604/30, 34, 101, 604/96, 102, 250; 606/192; 251/4–7

[56] References Cited

U.S. PATENT DOCUMENTS

| | | |
|---|---|---|
| Re. 33,219 | 5/1990 | Daniell et al. ............................ 251/7 |
| 1,880,948 | 10/1932 | Evennett . |
| 2,471,623 | 5/1949 | Hubbell ................................. 604/250 |
| 2,709,542 | 5/1955 | Eller et al. ............................ 604/250 |
| 3,812,841 | 5/1974 | Isaacson . |
| 4,148,319 | 4/1979 | Kasper et al. . |
| 4,211,233 | 7/1980 | Lin . |
| 4,350,161 | 9/1982 | Davis, Jr. . |
| 4,432,757 | 2/1984 | Davis, Jr. . |
| 4,579,554 | 4/1986 | Glassman . |
| 4,642,104 | 2/1987 | Sakamoto et al. . |
| 4,813,935 | 3/1989 | Haber et al. ............................ 604/99 |
| 4,932,938 | 6/1990 | Goldberg et al. . |
| 4,946,449 | 8/1990 | Davis, Jr. . |
| 5,004,454 | 4/1991 | Beyar et al. . |
| 5,030,199 | 7/1991 | Barwick et al. . |
| 5,041,092 | 8/1991 | Barwick . |
| 5,306,226 | 4/1994 | Salama . |
| 5,306,241 | 4/1994 | Samples . |
| 5,522,806 | 6/1996 | Schonbachler et al. ............... 604/34 |

*Primary Examiner*—Corrine M. McDermott
*Assistant Examiner*—Deborah Blyveis
*Attorney, Agent, or Firm*—Bachman & Lapointe, P.C.

[57] ABSTRACT

A urinary catheter includes a cannula having a urine passage, a urine inlet and a urine outlet and a valve positioned in the urine passage between the inlet and the outlet and including a compressible tube, and a member for releasably compressing the tube, the member for releasably compressing being biased toward a compressing position wherein the tube is compressed and flow through the tube is substantially blocked, and the member for releasably compressing being positionable to a released position at least partially releasing compression of the tube wherein flow through the tube is allowed.

24 Claims, 4 Drawing Sheets

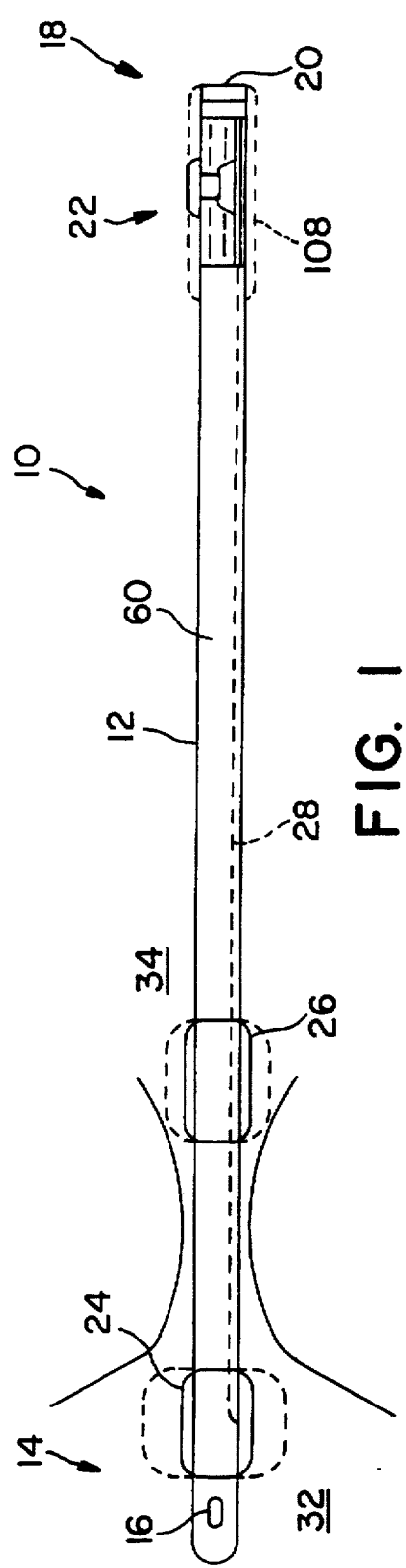
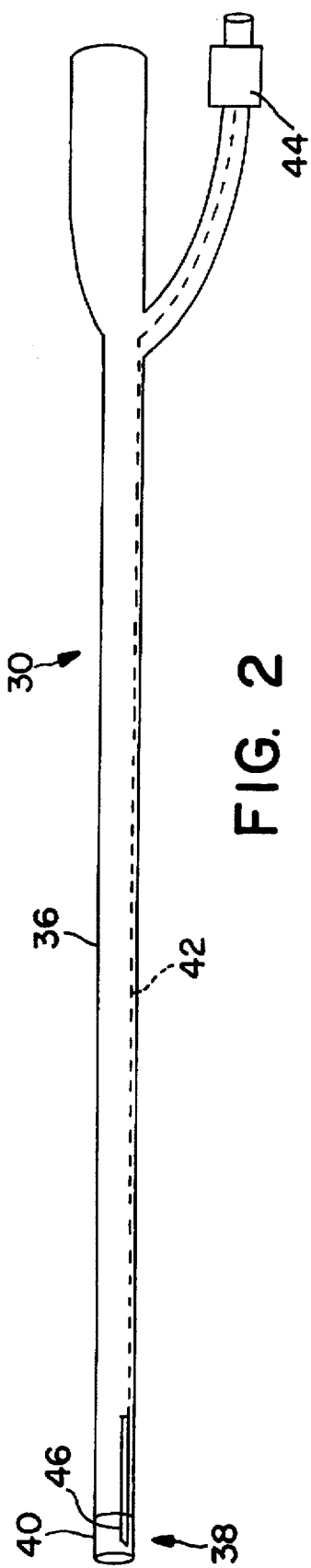
FIG. 1
FIG. 2

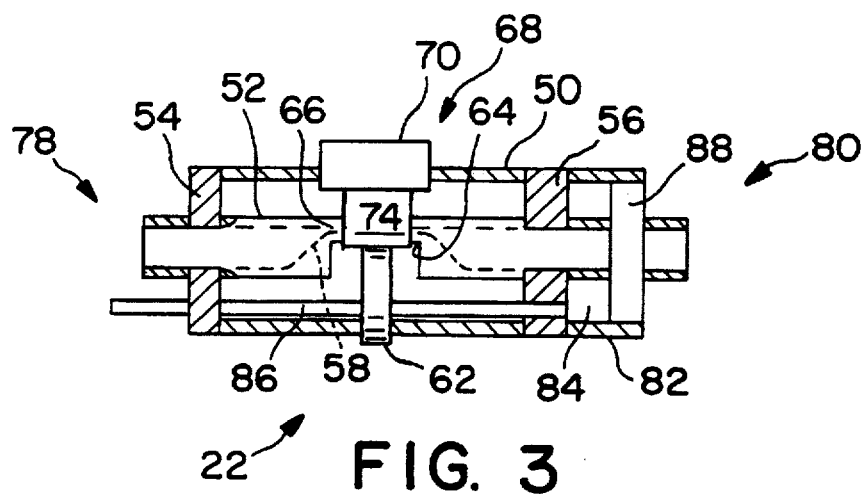
FIG. 3
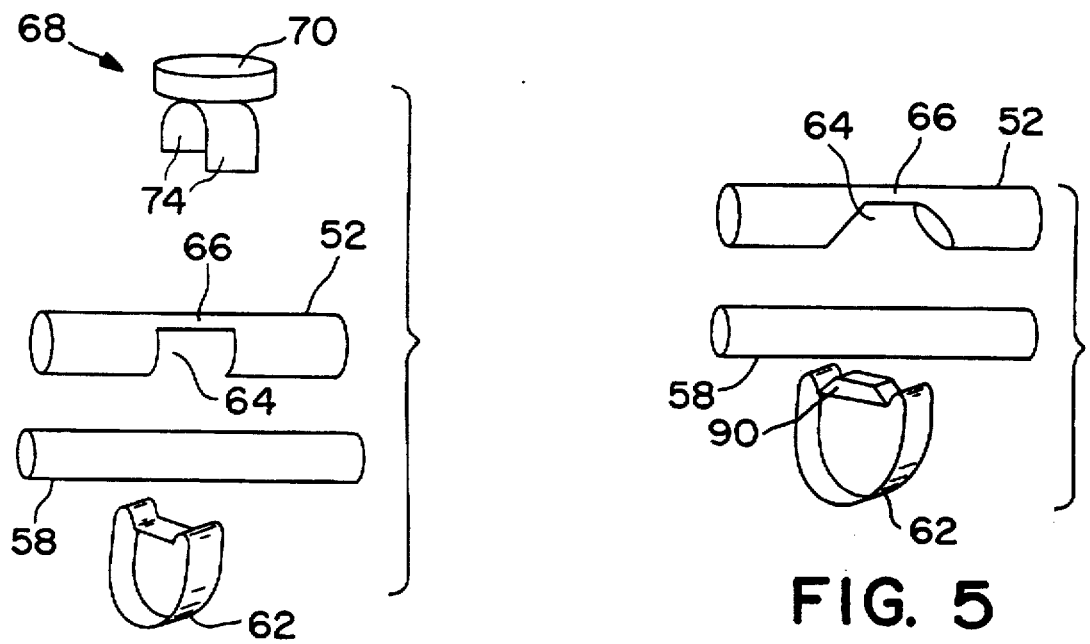
FIG. 4
FIG. 5
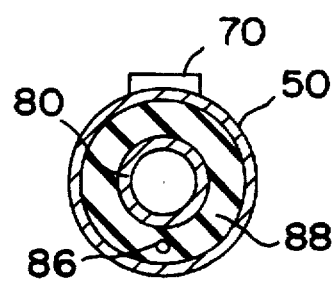
FIG. 6

INTERNAL URINARY CATHETER

CROSS REFERENCE TO DISCLOSURE DOCUMENT

This application is related to disclosure document Ser. No. 382,863 filed Oct. 12, 1995.

BACKGROUND OF THE INVENTION

The invention relates to an internal urinary catheter, especially an internal urinary catheter for male patients having obstructive uropathy or urinary incontinence.

Catheterization of the bladder with flexible rubber tubes to relieve obstructed urine flow in male patients is a well established procedure. Chronic obstruction may be treated by intermittent (several times per day) straight catheterization or by placement of an indwelling catheter. Intermittent self-catheterization is an uncomfortable procedure that also incurs the risk of repeated urinary infections. Conventional indwelling catheters invariably become colonized with bacteria and also require an attached collecting bag. Urinary incontinence is extremely difficult to treat; artificial sphincters must be surgically implanted and are prone to many complications.

Numerous attempts have been made at developing internal urinary catheters. However, these devices include complicated valve mechanisms and the like, which lead to complications during use of same, particularly with respect to complicated valve components which are exposed to urine during use and which increase the likelihood of bacteria colonization. The need remains for an internal urinary catheter having a simple but reliable valve structure.

It is therefore the primary object of the present invention to provide an internal urinary catheter having a reliable and easily operable valve which does not have complicated valve components exposed to urine during use.

It is a further object of the present invention to provide a urinary catheter having a valve which is easily operated by a patient.

It is a still further object of the present invention to provide a urinary catheter which can be reliably positioned with respect to the bladder and urethra.

It is another object of the invention to provide an internal urinary catheter having an insertion member for activating catheter retention members when the catheter is within the urethra.

It is still another object of the present invention to provide a method for catheterization and use of a catheter in accordance with the present invention.

Other objects and advantages of the present invention will appear hereinbelow.

SUMMARY OF THE INVENTION

In accordance with the present invention, the foregoing objects and advantages are readily attained.

According to the invention, a urinary catheter is provided which comprises a cannula having a urine passage, a urine inlet and a urine outlet and valve means positioned in said urine passage between said inlet and said outlet and comprising a compressible tube, and means for releasably compressing said tube, said means for releasably compressing being biased toward a compressing position wherein said tube is compressed and flow through said tube is substantially blocked, and said means for releasably compressing being positionable to a released position at least partially releasing compression of said tube wherein flow through said tube is allowed.

In further accordance with the invention, a valve for an internal urinary catheter is provided which comprises a passage for urine flow, a compressible tube positioned along said passage, and means for releasably compressing said compressible tube, said means for releasably compressing being biased toward a compressing position wherein said tube is compressed and flow through said tube is substantially blocked, and said means for releasably compressing being positionable to a released position at least partially releasing compression of said tube wherein flow through said tube is allowed.

In still further accordance with present invention, a method for controlling urine flow is provided which comprises the steps of providing a urine cannula having an inlet end having a urine inlet, an outlet end having a urine outlet and a valve for limiting flow from said urine inlet to said urine outlet, said valve comprising a compressible tube positioned along said cannula, and means for releasably compressing said compressible tube, said means for releasably compressing being biased toward a compressing position wherein said tube is compressed and flow through said tube is substantially blocked, and said means for releasably compressing being positionable to a released position at least partially releasing compression of said tube wherein flow through said tube is allowed, positioning said urine cannula in the urethra with said urine inlet in the bladder, and moving said means for releasably compressing to said released position so as to allow flow of urine from the bladder through said cannula and said compressible tube to said urine outlet, whereby said means for releasably compressing is isolated from urine flow through said valve.

Still further according to the invention, a method is provided for positioning an internal urinary catheter within the urethra, which method comprises the steps of providing a catheter comprising a urine passage, a urine inlet, a urine outlet, valve means for controlling urine flow from said urine inlet to said urine outlet, a bladder retention balloon positioned proximate to said urine inlet, a urethra retention balloon spaced toward said outlet end from said bladder retention balloon, and a balloon fluid passage communicating with said bladder retention balloon and said urethra retention balloon, positioning said catheter in the urethra with said urine inlet and said bladder retention balloon in the bladder adjacent the neck and orifice of the bladder, and with said urethra retention balloon in the urethra adjacent the neck and orifice of the bladder, and inflating said bladder retention balloon and said urethra retention balloon whereby said bladder retention balloon retains said urine inlet within the bladder and said urethra retention balloon retains said catheter within the urethra against back migration into the bladder.

BRIEF DESCRIPTION OF THE DRAWINGS

A detailed description of preferred embodiments of the invention follows, with reference to the attached drawings, wherein:

FIG. 1 is a side view of an internal urinary catheter according to the invention;

FIG. 2 is a side view of an insertion member for an internal urinary catheter according to the invention;

FIG. 3 is a side sectional view of a valve for an internal urinary catheter according to the invention;

FIG. 4 is an exploded view of certain elements of the valve mechanism of FIG. 3;

FIG. 5 is an exploded view of an alternate embodiment of the elements of FIG. 4;

FIG. 6 is an end view of the valve mechanism of FIG. 3 in accordance with the invention;

DETAILED DESCRIPTION

Figure 7:
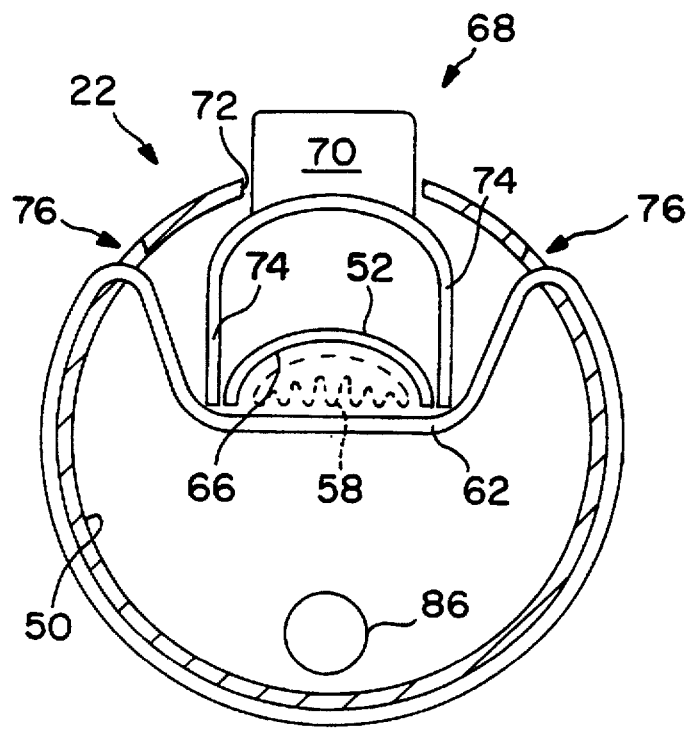
FIG. 7 is a sectional view of the valve of FIG. 3, in a compressed and closed position.

The invention relates to an internal urinary catheter, particularly a self contained internal urinary catheter for male patients particularly useful for treating obstructive uropathy or urinary incontinence. Referring to the drawings, catheter 10 in accordance with the present invention will be described.

FIG. 1 illustrates catheter 10 which includes a urine tube or cannula 12 having an inlet end 14, a urine inlet 16 at inlet end 14, an outlet end 18, a urine outlet 20 at outlet end 18, a valve mechanism 22 positioned along tube 12 for controlling flow from urine inlet 16 to urine outlet 20, a bladder retention balloon 24 positioned at inlet end 14, a urethra retention balloon 26 positioned generally at inlet end 14, and spaced toward outlet end 18 from bladder retention balloon 24, and a fluid passage 28 extending from outlet end 18 along tube 12 into communication with bladder retention balloon 24 and urethra retention balloon 26.

Urine tube 12 in accordance with the invention is preferably a generally flexible tube member made of suitable material and sized for positioning within the urethra of a patient to be treated with catheter 10 according to the invention. Urine inlet 16 at inlet end 14 of tube 12 may suitably be a number of ports or other structures suitable for allowing the inward flow of urine to be removed from the bladder. Outlet end 18 of tube 12 is preferably adapted to couple with an insertion/removal member 30 (FIG. 2) which will be described below. Tube 12 in accordance with the invention preferably has a substantially uniform shape and diameter along its length.

Valve mechanism 22 in accordance with the invention advantageously provides simple and reliable control of flow through urine tube 12. The specific details and operation of valve mechanism 22 in accordance with the invention will be described in further detail hereinbelow.

Bladder retention balloon 24 and urethra retention balloon 26 in accordance with the invention advantageously provide retention of catheter 10 in position as desired. When catheter 10 is inserted in the urethra of a patient, bladder retention balloon 24 maintains urine inlet 16 within the bladder (generally indicated at 32), and urethra retention balloon 26 prevents back migration of catheter 10 into bladder 32. As shown schematically in FIG. 1, bladder retention balloon 24 and urethra retention balloon 26 in accordance with the invention are preferably positioned for use with bladder retention balloon 24 to the bladder 32 side of the neck and orifice of bladder 32, and with urethra retention balloon 26 to the urethra side (generally indicated at 34) of the neck and orifice of bladder 32. In this manner, and advantageously, catheter 10 is securely retained in the proper position, and a seal is maintained between catheter 10 and the neck and orifice of bladder 32 so as to prevent flow of urine around the outside of catheter 10.

Referring now to FIG. 2, insertion/removal member 30 preferably includes an elongate and preferably flexible tube 36 preferably of substantially the same outside diameter as catheter 10. Tube 36 preferably has a coupling end 38 including a sleeve 40 for frictional engagement with outlet end 18 of catheter 10. Insertion/removal member 30 preferably includes a passage 42 in fluid communication with a source for providing and withdrawing balloon inflation fluid, which channel 42 may for example be connected to such a source through channel inlet port 44. Coupling end 38 preferably also includes a hollow needle member 46 in fluid communication with channel 42 for establishing inflation fluid communication with fluid passage 28 of catheter 10 as will be further discussed below.

Referring back to FIG. 1, valve mechanism 22 of the illustrated embodiment of the present invention is positioned directly at outlet end 18 of catheter 10. In this embodiment, valve mechanism 22 includes urine outlet 20 which also serves as the member for coupling with coupling end 38 of insertion/removal member 30. FIGS. 3–6 to be discussed below describe features of valve mechanism 22. It should of course be noted that urine outlet 20 and its associated elements could be provided at outlet end 18 of catheter 10, with valve mechanism 22 provided separately and, optionally, spaced from outlet end 18 of catheter 10 if desired.

Referring now to FIG. 3, valve mechanism 22 preferably includes a housing 50 preferably having substantially the same outside diameter as urine tube 12. A valve passage or sleeve 52 may suitably be provided within housing 50, for example supported by annular collars 54, 56. In further accordance with the invention, valve 22 further includes a compressible tube 58 disposed within valve passage 52 and arranged for sealing connection with a urine flow passage 60 (FIG. 1) of urine tube 12.

In accordance with the invention, a compression member 62 such as an elastic band as illustrated in FIG. 3 is positioned relative to housing 50 so as to compress compressible tube 58 and thereby block flow through compressible tube 58 so as to close valve 22. As shown in FIG. 3, valve passage 52 preferably has a cutout portion 64 defining a backing member 66 positioned substantially adjacent to compressible tube 58 as shown. Elastic member 62 in accordance with the invention is preferably positioned within cutout portion 64 and stretched or biased toward backing member 66 with compressible tube 58 therebetween so as to compress compressible tube 58 as desired.

Still referring to FIG. 3, a push member 68 is preferably provided, movably or slidably positioned relative to housing 50, and positioned substantially adjacent to or contacting elastic member 62, most preferably in close proximity to backing member 66. In accordance with the invention, push member 68 is movable relative to housing 50 and backing member 66 between a released position illustrated in FIG. 3 wherein elastic member 62 is in a relatively relaxed state and compresses compressible tube 58 and blocks flow through valve 22, and a biased position wherein push member 68 deflects or stretches elastic member 62 away from backing member 66 into a relatively stretched state so as to at least partially release compression of compressible tube 58 and thereby allow flow through compressible tube 58 and, thereby, valve 22. Push member 68 is preferably movable relative to housing 50 of valve 22 in a direction substantially perpendicular to the flow passage of valve 22 so that application of a radially inwardly directed force serves to move push member 68 as desired. The function of push member 68, elastic member 62 and compressible tube 58 will be further described below in connection with FIGS. 7 and 8.

Referring to FIG. 4, an exploded view of push member 68, valve passage 52, compressible tube 58 and elastic member 62 is provided. Push member 68 preferably comprises a member 70 which is slidably positioned in a port 72 (FIG. 3) of housing 50 and which is arranged so as preferably to extend radially outwardly from housing 50. Push member 68 preferably further includes arm members 74 extending from member 70 to interact with elastic member 62, for deflecting elastic member 62 away from compressible tube 58 to at least partially release compression of tube 58 when desired. As shown, arm members 74 may preferably extend away from member 70 at a lateral spacing sufficient to extend to either side of backing member 66 of flow passage 60.

Elastic member 62 is preferably positioned relative to flow passage 60 so as to be positioned across backing member 66. In FIG. 4, elastic member 62 is shown in a shape induced by a combination of housing 50 and backing member 66 as will be further described.

Figure 8:
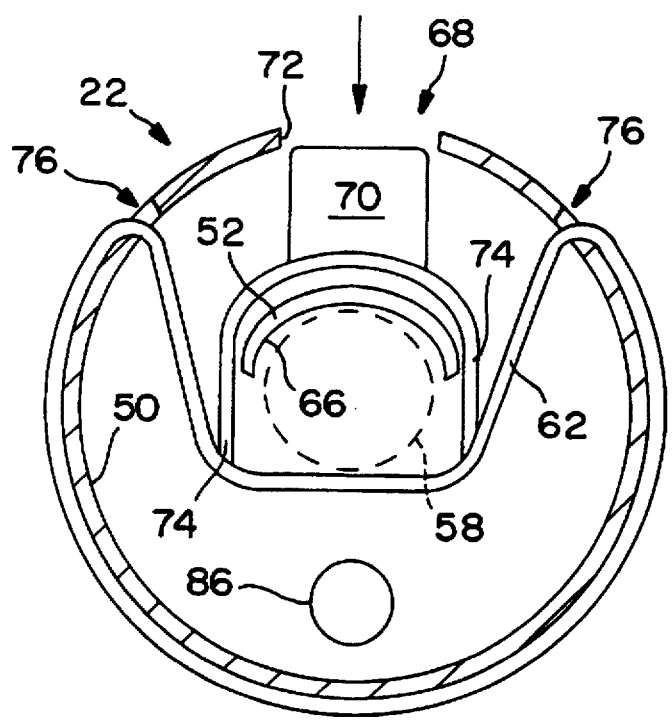
FIG. 8 is a sectional view similar to FIG. 7, with the valve in an open or released position.
Figure 9A:
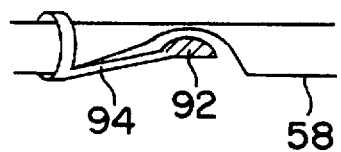
FIGS. 9a and 9b, 10a and 10b, 11a and 11b, and 12a and 12b illustrate alternative embodiments of elements of the valve member according to the invention.
Figure 9B:
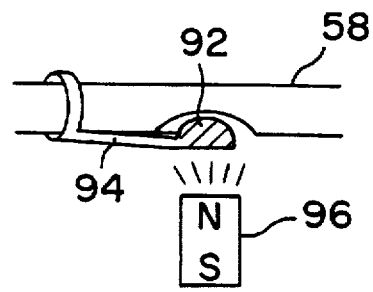

Referring to FIGS. 7 and 8, the position and operation of push member 68, flow passage 52, compressible tube 58 and elastic member 62 is readily apparent. FIG. 7 shows housing 50 having gaps 76 through which elastic member 62 is positioned. Elastic member 62 in accordance with the invention is preferably stretched around housing 50, through gaps 76, and across backing member 66 with compressible tube 58 positioned therebetween. As shown, push member 68 is preferably slidably positioned relative to housing 50 and backing member 66 with arm members 74 preferably contacting or in close association with elastic member 62 to each side of backing member 66. In this manner, radially inward movement or deflection of push member 68 as shown in FIG. 8 serves to stretch elastic member 62 and deflect same away from backing member 66, releasing compression of compressible tube 58 and thereby allowing flow therethrough.

With reference to FIGS. 3, 7 and 8, it should be readily apparent that flow through valve 22 is accomplished while isolating the various components of valve 22 from contact with urine, thereby greatly reducing the chance for bacterial colonization of catheter 10 in accordance with the invention. Specifically, compressible tube 58 carries urine flow from an inlet end 78 of valve 22 to an outlet end 80 of valve 22 without contact of urine with, for example, push member 68, elastic member 62, backing member 66 and the like.

Returning to FIG. 3, valve 22 preferably further includes a tubular portion 82 which may be a separate element or an extension of housing 50, which extends beyond collar 56 so as to define an annular space or chamber 84 between tubular portion 82 and valve passage 52. Valve 22 preferably further includes a balloon inflation fluid passage 86 which communicates with space 84 and extends from valve 22 into fluid communication with fluid passage 28. Passage 86 may suitably comprise a hollow needle member or the like preferably supported in apertures positioned in annular collars 54, 56 for stability. At outlet end 80 of valve 22, and corresponding to outlet end 18 of catheter 10, a self-sealing diaphragm 88 is preferably positioned so as to seal annular space 84. Diaphragm 88 is preferably a ring-shaped member sized to provided sealing contact with valve passage 52 and tubular portion 82. Diaphragm 88 advantageously allows piercing by hollow needle member 46 so as to allow fluid communication between annular space 84 and channel 42 of insertion/removal member 30. Further, self-sealing diaphragm 88 advantageously seals after removal of hollow needle member 46, thereby sealing balloon inflation fluid within bladder retention balloon 24 and urethra retention balloon 26 as desired. This is advantageous in accordance with the invention as the disclosed structure allows balloons 24, 26 to be inflated while catheter 10 is in position for use, entirely within the urethra.

In further accordance with the invention, and as further illustrated by the end view of FIG. 6, the provision of annular space 84 and self-sealing diaphragm 88 makes re-connection of coupling end 38 of insertion/removal member 30 with outlet end 18 of catheter 10 more readily accomplished. Specifically, coupling end 38 with hollow needle member 46 can be re-coupled with outlet end 18 of catheter 10, which corresponds in this embodiment with outlet end 80 of valve 22, regardless of the radial orientation of needle member 46 with respect to diaphragm 88 or passage 86. Referring specifically to FIG. 6, re-connection of hollow needle member 46 with passage 86 may be accomplished by piercing diaphragm 88 with hollow needle member 46 at any position in diaphragm 88, and, advantageously, not necessarily in a position aligned with passage 86.

FIGS. 7 and 8 show backing member 66 of flow passage 60 having a semi-circular shape defining a concave contour facing compressible tube 58. In accordance with an alternative embodiment of the invention, elastic member 62 may be provided having a convex contour substantially matching the concave contour of backing member 66 so as to provide a more effective compression and blockage of flow through compressible tube 58. As shown in FIG. 5, for example, elastic member 62 may be provided with a thickened portion 90 arranged to mate with backing member 66 as desired. Of course, it should be appreciated that backing member 66 may be provided having numerous different types or shapes of contour, and that elastic member 62 according to the invention could likewise be provided with a matching contour as desired.

FIGS. 9–12 illustrate several alternative embodiments of structure for compressing compressible tube 58 as desired in accordance with the invention. Referring to FIGS. 9a–9b, a magnetic compression member 92 may be provided, and positioned at the end of an elastic arm 94 substantially rigidly mounted, for example, to flow passage 60 or any other substantially rigid structure of valve 22. Arm 94 in accordance with this embodiment is preferably biased to an inwardly directed position as shown in FIG. 9a, wherein compression member 92 cooperates with a backing member (not shown) to compress compressible tube 58 as desired. In accordance with this embodiment, positioning of a magnetic releasing member 96 (FIG. 9b) within sufficiently close proximity to magnetic compression member 92 results in attraction of compression member 92 toward magnetic releasing member 96 so as to deflect arm 94 and, thereby, magnetic compression member 92 away from the backing member, thereby at least partially releasing compression and blocking of compressible tube 58.

Figure 10A:
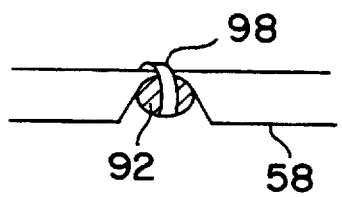
Figure 10B:
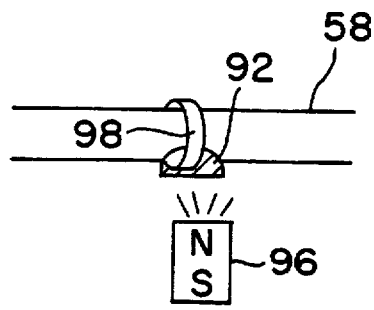

FIGS. 10a–10b illustrate a similar alternative embodiment wherein magnetic compression member 92 is elastically held with reference to the backing member (not shown) by an elastic band member 98 positioned around the backing member, compressible tube 58 and magnetic compression member 92. In a similar manner to the embodiment of FIGS. 9a–9b, positioning of a magnetic release member 96 in sufficiently close proximity results in an attraction of magnetic compression member 92 toward magnetic release member 96 as shown, thereby stretching elastic band member 98 and at least partially releasing compression of compressible tube 58.

Figure 11A:
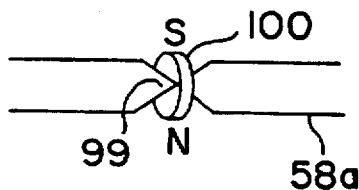
Figure 11B:
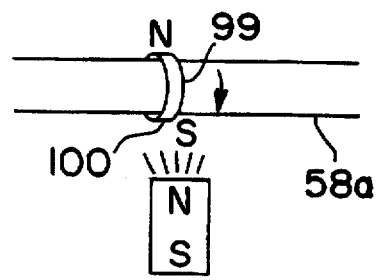

Referring to FIGS. 11a–11b, a still further alternative embodiment of the invention with respect to the compression and releasing of compression of compressible tube 58 is illustrated. As shown, compressible tube 58a may be provided having a section 99 biased toward a twisted and, thereby, compressed and closed position. A polar magnetic member 100 may suitably be provided, preferably mounted in close proximity to section 99 and having north and south poles as illustrated in the drawing, whereby positioning of magnetic release member 96 as shown in FIG. 11b attracts north pole of magnetic member 100 thereby twisting compressed section 99 to a straightened position as shown in FIG. 11b, wherein compression of compressible tube 58a is released, and flow is allowed.

Figure 12A:
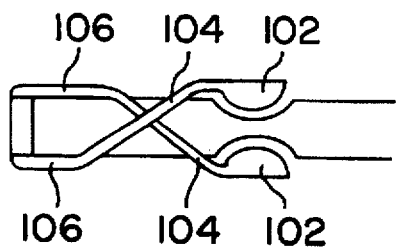
Figure 12B:
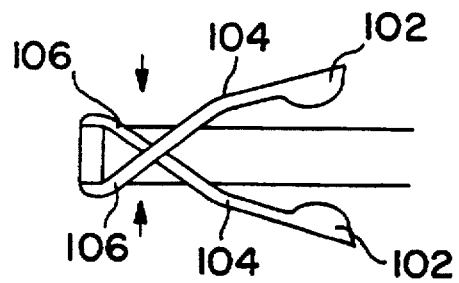

FIGS. 12a–12b illustrate still another alternative embodiment of the invention drawn to an alternative structure for compressing compressible tube 58. In accordance with the embodiment of FIGS. 12a–12b, two compression members 102 are provided, preferably positioned at the ends of flexible arms 104. As shown in FIG. 12a, arms 104 may be spiralled a half rotation with respect to compressible tube 58 so as to arrange compressible members 102 in a position whereby a compressive force directed at base portions 106 of arms 104 results in a spreading of compression members 102 as shown in FIG. 12b.

With reference to the above described various embodiments of the present invention for applying and releasing compression to and from compressible tube 58, it should be readily apparent that each embodiment allows for reliable and simple compression of tube 58 to provide effective blockage of flow through valve 22. Further, release of compression of tube 58 is accomplished in each embodiment through the simple positioning of a magnetic release member, or through the application of a simple radially inwardly directed compressive force which is both dictated by the anatomy in which catheter 10 is positioned and used and readily accomplished with catheter 10 of the present invention.

In accordance with the invention, a catheter 10 is positioned for use as follows.

Initially, catheter 10 is coupled with insertion/removal member 30 by connecting coupling end 38 to outlet end 80 of valve 22. In this connected position, sleeve 40 is positioned over outlet end 80, and hollow needle member 46 pierces diaphragm 88 so that fluid passage 28 and, thereby, balloons 24, 26 are in fluid communication with hollow needle 46 and, thereby, a source of balloon inflation fluid. The assembly is then inserted into the urethra with inlet end 16 of catheter being inserted first. Catheter 10 is inserted until urine inlet 16 is positioned within bladder 32 as shown schematically in FIG. 1, with bladder retention balloon 24 positioned within bladder 32 and urethra retention balloon 26 positioned just inside urethra 34 as schematically shown in FIG. 1. At this point, balloon inflation fluid is introduced through channel 42, through hollow needle member 46 into annular space 84, and into fluid passage 28, eventually reaching balloons 24, 26 so as to inflate same to the desired size. In this regard, bladder retention balloon 24 is preferably provided from a material which will allow a relatively greater expansion than urethra retention balloon 26 in response to the same pressure of inflation fluid. For example, with catheter 10 having a size of approximately 16 French, urethra retention balloon 26 may be expandable, for example, to about 22 French, while bladder retention balloon is expandable to a somewhat larger size.

Upon proper inflation of balloons 24, 26, catheter 10 is properly retained with respect to bladder 32 and urethra 34, and is thereby held properly within bladder 32 against back migration of the entire device into bladder 32. At this point, insertion/removal member 30 is released from connection with catheter 10, and hollow needle member 46 is withdrawn from self-sealing diaphragm 88, which seals upon such removal and thereby seals balloon inflation fluid within balloons 24, 26 as desired. Insertion/removal member 30 is then removed from the urethra, and catheter 10 is properly inserted for use.

Valve 22 in accordance with the invention can then be operated, depending upon the embodiment in use, through application of compressive force or proper positioning of a magnetic means, so as to release compression of compressible tube 58 within valve 22, and thereby allow flow of urine from bladder 32, into urine inlet 16, through urine tube 12 and valve 22 to urine outlet 20 as desired.

It should be appreciated that catheter 10 in accordance with the invention is designed so as to provide a relatively long-term correction to the above-noted uropathy and incontinence problems. In this regard, a membrane 108 or other member may suitably be positioned over valve 22, for example as shown in FIG. 1. This is advantageous so as to limit the exposure of various components of valve 22 to contact with urethra 34 as well.

It should also be appreciated that, because catheter 10 is designed as an indwelling member having minimal parts exposed to urine flow, the colonization of bacteria and other causes of infection are significantly impeded or removed.

If it is desired to remove catheter 10 after installation, insertion/removal member 30 is re-inserted into urethra 34 so as to connect coupling end 38 with outlet end 80, and reintroduce hollow needle member 46 through diaphragm 88 into annular space 84. Once this connection is completed, balloon inflation fluid can be removed from balloons 24, 26 so as to deflate same, and coupled catheter 10 and insertion/removal member 30 can be removed from bladder 32 and urethra 34 as desired.

In accordance with the foregoing, it should be readily apparent that a catheter, a valve for a catheter, and methods for using same have been disclosed in accordance with the invention so as to accomplish each and every object set forth hereinabove.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. An internal urinary catheter, comprising:
   a cannula having an external diameter, a urine passage, a urine inlet and a urine outlet; and
   valve means positioned along said urine passage between said inlet and said outlet and comprising a compressible tube, and means for releasably compressing said tube, said valve means having an external diameter substantially the same as said external diameter of said cannula, said means for releasably compressing being biased toward a compressing position wherein said tube is compressed and flow through said tube is substantially blocked, and said means for releasably compressing being positionable to a released position at least partially releasing compression of said tube wherein flow through said tube is allowed.

2. A catheter according to claim 1, further comprising retention means for retaining said inlet end of said cannula with respect to a bladder of a patient.

3. A catheter according to claim 2, wherein said retention means comprises inflatable retention means, a fluid channel disposed along said cannula and through said valve and communicating with said inflatable retention means, and fluid introduction means associated with said fluid channel for introducing fluid into said fluid channel whereby said inflatable retention means can be inflated for securing said cannula in position.

4. A catheter according to claim 3, wherein said means for introducing comprises a chamber communicated with said fluid channel, and means for communicating a source of fluid with said chamber.

5. A catheter according to claim 4, wherein said means for communicating comprises a self-sealing diaphragm positioned over said chamber.

6. A catheter according to claim 5, wherein said source of fluid comprises a hollow member for puncturing said self-sealing diaphragm so as to introduce said fluid to said chamber, whereby said hollow member can be introduced at any point in said diaphragm into said chamber to communicate with said fluid channel.

7. A catheter according to claim 6, wherein said chamber comprises a tubular member positioned around said cannula so as to define an annular space wherein said fluid channel communicates with said annular space, and wherein said self-sealing diaphragm comprises a ring positioned over said cannula substantially adjacent said annular space.

8. A catheter according to claim 7, further comprising insertion means for inserting said cannula in the urethra of a patient and for inflating said inflatable retention means when said outlet end of said cannula is within the urethra.

9. A catheter according to claim 8, wherein said insertion means comprises a sleeve member and coupling means for coupling said sleeve member to said outlet end, and wherein said means for inflating comprises means associated with said coupling means for introducing fluid into said filling channel.

10. A catheter according to claim 9, wherein said means for introducing comprises hollow means for puncturing said diaphragm, said hollow means being connected to a source of fluid.

11. A catheter according to claim 2, wherein said retention means comprises a bladder retention member positioned along said cannula at said inlet end, and a urethral retention member spaced toward said outlet end from said bladder retention member and spaced toward said inlet end from said valve means.

12. A catheter according to claim 11, wherein said bladder retention member comprises a bladder retaining balloon, and said urethral retention member comprises a urethral retaining balloon, and further comprising fluid channel means disposed along said cannula and communicating with said bladder retaining balloon and said urethral retaining balloon and fluid introduction means for introducing fluid into said fluid channel means whereby said bladder retaining balloon and said urethral retaining balloon can be inflated for securing said cannula in position.

13. A catheter according to claim 12, wherein said fluid channel means comprises a fluid channel communicated with both of said bladder retaining balloon and said urethral retaining balloon.

14. A catheter according to claim 12, wherein said bladder retaining balloon and said urethral retaining balloon are provided from materials having different elasticity whereby said bladder retaining balloon inflates to a size greater than said urethral retaining balloon when subjected to fluid at the same pressure.

15. A catheter according to claim 3, further comprising insertion means for inserting said cannula in the urethra of a patient and for inflating said inflatable retention means when said outlet end of said cannula is within the urethra.

16. A catheter according to claim 15, wherein said insertion means comprises a sleeve member and coupling means for coupling said sleeve member to said outlet end, and wherein said means for inflating comprises means associated with said coupling means for introducing fluid into said fluid channel.

17. A catheter according to claim 1, wherein said valve means further comprises a sleeve positioned along said cannula and having a cutout portion, said compressible tube being positioned within said sleeve, and wherein said means for releasably compressing is biased against said tube at said cutout so as to block flow through said tube.

18. A catheter according to claim 17, wherein said valve means further comprises elastic means positioned across said cutout to compress said tube, and means for pushing said elastic means away from said cutout whereby compression of said tube is at least partially released.

19. A catheter according to claim 18, wherein said means for pushing comprises a push member slidably positionable relative to said sleeve and having at least one arm member contacting said elastic means substantially adjacent to said cutout whereby sliding said push member relative to said sleeve positions said means for releasably compressing between said compressing position and said released position.

20. A catheter according to claim 19, wherein said elastic member biases said push member into said compressing position.

21. A catheter according to claim 17, wherein said sleeve has a contour at said cutout, and wherein said means for releasably compressing includes a contact portion shaped to substantially match said contour whereby blockage of flow in said compressed position is enhanced.

22. A catheter according to claim 1, further comprising a membrane positioned over said valve means so as to limit exposure of said valve means to contact with a urethra during use.

23. A urinary catheter, comprising:
a cannula having a urine passage, a urine inlet and a urine outlet; and
valve means positioned along said urine passage between said inlet and said outlet and comprising a housing positioned along said cannula, a sleeve positioned within said housing and having a cutout portion, a compressible tube positioned within said sleeve, and means contacting said compressible tube through said cutout portion for releasably compressing said tube, said means for releasably compressing being biased toward a compressing position wherein said tube is compressed and flow through said tube is substantially blocked, and said means for releasably compressing being positionable to a released position at least partially releasing compression of said tube wherein flow through said tube is allowed.

24. A urinary catheter, comprising:
a cannula having a urine passage, a urine inlet and a urine outlet;
valve means positioned along said urine passage between said inlet and said outlet and comprising a compressible tube, and means for releasably compressing said tube, said means for releasably compressing being biased toward a compressing position wherein said tube is compressed and flow through said tube is substantially blocked, and said means for releasably compressing being positionable to a released position at least partially releasing compression of said tube wherein flow through said tube is allowed;

retention means for retaining said inlet end of said cannula with respect to a bladder of a patient;

said retention means comprising inflatable retention means, a fluid channel disposed along said cannula and communicating with said inflatable retention means, and fluid introduction means associated with said fluid channel for introducing fluid into said fluid channel whereby said inflatable retention means can be inflated for securing said cannula in position; and insertion means for inserting said cannula in the urethra of a patient and for inflating said inflatable retention means when said outlet end of said cannula is within the urethra.

* * * * *